US00PP10047P

United States Patent [19]

Polys

[11] Patent Number: Plant 10,047

[45] Date of Patent: Sep. 30, 1997

[54] CHRYSANTHEMUM PLANT NAMED 'CREAM DIAMOND'

[75] Inventor: Susan M. Polys, Salinas, Calif.

[73] Assignee: Yoder Brothers, Inc., Barberton, Ohio

[21] Appl. No.: 605,729

[22] Filed: Feb. 22, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

| | | | |
|---|---|---|---|
| P.P. 8,059 | 12/1992 | VandenBerg | Plt./77 |
| P.P. 8,364 | 9/1993 | VandenBerg | Plt./78 |
| 4,616,099 | 10/1986 | Sparkes | 47/58 |

OTHER PUBLICATIONS

Broertjes, et al., 1980, "A mutant of a mutant of a . . . Irradiation of progressive radiation-induced mutants in a mutation breeding programme with *Chrysanthemum morifolium*", Euphytica, 29:525–530.

Gosling, ed., 1979, "The Chrysanthemum Manual 6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of Chrysanthemums", Euphytica, 15:156–162.

Dowrick, et al., 1966, "The induction of mutations in Chrysanthemum using X-and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Cream Diamond particularly characterized by its flat capitulum form; decorative capitulum type; cream-yellow ray floret color; diameter across face of capitulum of 133 to 159 mm when fully opened, when grown as a pinched disbudded pot mum; photoperiodic flowering response of 49 to 57 days after start of short days; plant height, with 15 to 18 long days after sticking unrooted cuttings and with 1 to 3 applications of 2500 ppm B-9 SP ranges from 20 to 28 cm when grown as a pinched pot mum with 4 cuttings in a 15 cm pot; branching pattern is spreading, each plant having 5 to 6 laterals after pinch; and recommended as a disbudded pot mum.

1 Drawing Sheet

The present invention comprises a new and distinct cultivar of Chrysanthemum, botanically known as *Dendranthema grandiflora,* and referred to by the cultivar name Cream Diamond.

Cream Diamond, identified as 4001 (85-789G02), is a product of a mutation induction program. The new cultivar was discovered and selected by inventor Susan M. Polys on May 21, 1993 in a controlled environment in Salinas, Calif. as one flowering plant within a flowering block established as rooted cuttings from stock plants which had been exposed as unrooted cuttings to an X-ray source of 1750 rads in Fort Myers, Fla. on Nov. 19, 1992. The irradiated parent cultivar was the cultivar White Diamond, disclosed in U.S. Plant Pat. No. 8,059, and described as a flat decorative disbud pot mum with a white flower color and a cream center of the flower.

The irradiation program resulting in Cream Diamond had as its primary objective the expansion of color ranges of the parent cultivar. The irradiation program comprised irradiation of cuttings of the parent cultivar at irradiation levels of 1500, 1750 and 2000 rads. A total of 1484 cuttings harvested from a total of 225 irradiated plants were planted on Mar. 8, 1993. Of these, 35 initial selections were made, which selections were then revegetated and reflowered. Three consecutive flowerings resulted in discarding 34 of the original 35 selections on Jan. 24, 1994. Two of the original selections were reselected on Jan. 3, 1994, after which the original selections were discarded. The 1 remaining original selection and the 2 reselections were maintained as PIs (Possible Introductions) and further trialed in Salinas, Calif. and Leamington, Ontario, Canada, ultimately resulting in discarding one reselection on Dec. 2, 1994, one original selection on Mar. 29, 1995, and the decision to introduce the one remaining reselection as Cream Diamond.

The first act of asexual reproduction of Cream Diamond was accomplished when vegetative cuttings were taken from the initial selection in July of 1993 in a controlled environment in Salinas, Calif., by technicians working under supervision of Susan M. Polys.

Horticultural examination of controlled flowerings of successive plantings has shown that the unique combination of characteristics as herein disclosed for Cream Diamond are firmly fixed and are retained through successive generations of asexual reproduction.

Cream Diamond has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Cream Diamond, which, in combination, distinguish this Chrysanthemum as a new and distinct cultivar:

1. Flat capitulum form.
2. Decorative capitulum type.
3. Cream-yellow ray floret color. 4. Diameter across face of capitulum of 133 to 159 mm when fully opened, when grown as a pinched disbudded pot mum.
5. Photoperiodic flowering response of 49 to 57 days after start of short days.
6. Plant height, with 15 to 18 long days after sticking unrooted cuttings and with 1 to 3 applications of 2500 ppm B-9 SP ranges from 20 to 28 cm when grown as a pinched pot mum with 4 cuttings in a 15 cm pot.

7. Branching pattern is spreading, each plant having 5 to 6 laterals after pinch.

8. Recommended as a disbudded pot mum.

The accompanying photographic drawing is a side view of Cream Diamond, grown as a disbudded pot mum with 4 cuttings in a 15 cm pot, with the colors being as nearly true as possible with illustrations of this type.

Of the commercial cultivars known to the inventor, the most similar in comparison to Cream Diamond is the parent cultivar White Diamond. All traits of Cream Diamond are similar to those of White Diamond, except for the ray floret color. The ray floret color of Cream Diamond is cream-yellow (R.H.S. 5D), while the ray floret color of White Diamond is described as white (R.H.S. 155D), with a cream (R.H.S. 4D) center of the flower.

In the following description color references are made to The Royal Horticultural Society Colour Chart. The color values were determined on plant material grown as a pinched pot mum with 4 cuttings in a 15 cm pot in Salinas, Calif. on May 17, 1995.

Classification:

*Botanical.*—*Dendranthema grandiflora* cv Cream Diamond.

*Commercial.*—Flat decorative disbud pot mum.

Inflorescence

A. Capitulum:

*Form.*—Flat.

*Type.*—Decorative.

*Diameter across face.*—133 to 159 mm when fully opened.

B. Corolla of ray florets:

*Color (general tonality from a distance of three meters).*—Cream-yellow.

*Color (upper surface).*—5D.

*Color (under surface).*—4D.

*Shape:* Straight, cross section concave, pointed petal tips.

C. Corolla of disc florets:

*Color (mature).*—13B to 14B.

*Color (immature).*—144B to 144C.

D. Reproductive organs:

*Androecium.*—Present on disc florets only; very few disc florets, no pollen.

*Gynoecium.*—Present on both ray and disc florets.

Plant

A. General appearance:

*Height.*—20 to 28 cm when grown as a pinched pot mum with 15 to 18 long days after sticking unrooted cuttings prior to start of short days and with 1 to 3 applications of 2500 ppm B-9 SP.

*Branching pattern.*—Spreading, with 5 to 6 laterals after pinch.

B. Foliage:

*Color (upper surface).*—147A.

*Color (under surface).*—148B.

*Shape.*—Deeply lobed and strongly serrated.

What is claimed is:

1. A new and distinct Chrysanthemum plant named Cream Diamond, as described and illustrated.

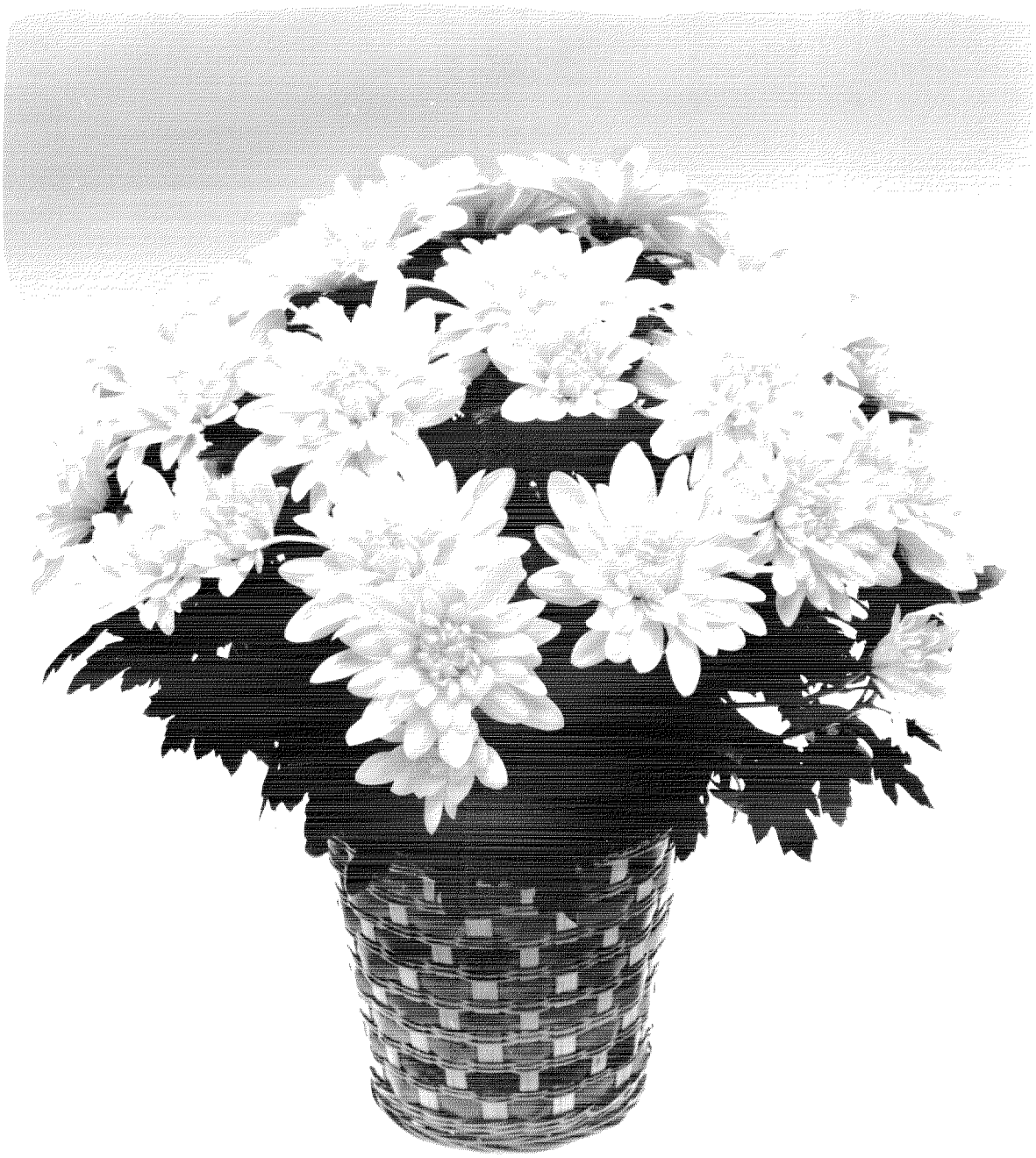

* * * * *